(12) United States Patent
Mitchell

(10) Patent No.: US 9,066,950 B2
(45) Date of Patent: Jun. 30, 2015

(54) ANALGESIC COMPOSITIONS

(75) Inventor: Odes W. Mitchell, Arlington, TX (US)

(73) Assignee: GM Pharmaceuticals, Inc., Arlington, TX (US)

( * ) Notice: Subject to any disclaimer, the term of this patent is extended or adjusted under 35 U.S.C. 154(b) by 616 days.

(21) Appl. No.: 12/715,954

(22) Filed: Mar. 2, 2010

(65) Prior Publication Data

US 2010/0298258 A1    Nov. 25, 2010

Related U.S. Application Data

(60) Provisional application No. 61/180,209, filed on May 21, 2009.

(51) Int. Cl.
| | | |
|---|---|---|
| A61K 31/70 | (2006.01) | |
| A61K 31/522 | (2006.01) | |
| A61K 31/60 | (2006.01) | |
| A61K 31/714 | (2006.01) | |

(52) U.S. Cl.
CPC .............. *A61K 31/522* (2013.01); *A61K 31/60* (2013.01); *A61K 31/714* (2013.01)

(58) Field of Classification Search
USPC ....................................... 514/52, 263.34, 165
See application file for complete search history.

(56) References Cited

U.S. PATENT DOCUMENTS

| | | | |
|---|---|---|---|
| 4,479,956 A | 10/1984 | Sunshine et al. | |
| 6,312,736 B1 * | 11/2001 | Kelly et al. | ............ 424/734 |
| 6,579,857 B1 * | 6/2003 | Lind et al. | ............ 514/46 |
| 2005/0148674 A1 | 7/2005 | Tang et al. | |
| 2007/0190153 A1 | 8/2007 | Farber | |

FOREIGN PATENT DOCUMENTS

EP    1103258 A1 *    5/2001

OTHER PUBLICATIONS

Ward et al. in Pain 44(2), 1991, 151-155.*
Jurna, I. in Schmerz. 1998 12(2):136-41.*
Codispoti et al. in Headache:The Journal of Head and Face Pain, 41(7), 665-679 (2001).*
'Guarana' in www.raysahelian.com/guarana.html (Mar. 2008).*
Brüggemann et al. in Klin. Wochenschr. 1990 68(2):116-120.*
Reyes-Garcia et al. in Current Topics in Pharmacology 10, 1-31 (2006).*
Ward et al. in Pain 44(2), 151-155 (1991).*
Bruggemann, G., et al. Results of a Double-Blind Study of Diclofenac + Vitamin B1, B6, B12 versus Diclofenac in patients with acute pain of the lumbar vertebrae. A multicenter study. Jan. 1990. vol. 68, No. 20, pp. 116-120: Abstract.
Lee W. Young, PCT International Search Report, Jul. 9, 2010.

* cited by examiner

*Primary Examiner* — James O Wilson
*Assistant Examiner* — Oluwafemi Masha
(74) *Attorney, Agent, or Firm* — Winstead PC

(57) ABSTRACT

Embodiments of the invention relates to pharmaceutical compositions for use in the treatment of pain and inflammation in mammals, including humans, by administering compositions comprising i) an effective amount of an analgesic having an optional anti-inflammatory effect; (ii) an amount of caffeine effective in enhancement of pain relief; and, (iii) an amount of B vitamins effective in enhancement of pain relief.

10 Claims, No Drawings

ANALGESIC COMPOSITIONS

CROSS-REFERENCES TO RELATED APPLICATIONS

This patent application claims priority to U.S. Provisional Application No. 61/180,209, filed May 21, 2009, which is fully incorporated by reference herein.

FIELD OF THE INVENTION

The present invention relates to pharmaceutical compositions comprising analgesics, caffeine and vitamins and to methods of using the compositions to hasten the onset of an analgesic and/or anti-inflammatory response and to enhance an analgesic and/or anti-inflammatory response.

BACKGROUND OF THE INVENTION

Statistics indicate that each year 550 million workdays are lost in the U.S. because of pain-related issues—roughly, 155 million workdays are lost because of headaches, 107 million workdays are lost due to joint pain, 98 million workdays are lost due to stomach pain, 89 million workdays are lost due to back pain, 58 million workdays are lost to muscular pain, 22 million workdays are lost to menstrual pain and 13 million workdays are lost to dental pain.

The non-steroidal anti-inflammatory drugs (NSAIDs) have been utilized in the treatment of pain/inflammation and a number of other symptoms including stiffness that are associated with painful conditions affecting muscles, bones, and joints. NSAIDs have been prescribed to relieve back pain, gout, headaches, mild pain following surgery, and pain from soft tissue injuries such as sprains and strains. NSAIDs are generally used to treat pain, fever, swelling and inflammation from medical conditions, including various types of arthritis, menstrual cramps and other mild to moderate pain. NSAIDs are within the broader class of non-narcotic analgesics. NSAIDs are generally considered to exert their effect by blocking the production of prostaglandins at the site of pain, irritation, or injury so that the pain signal does not reach the brain. NSAIDs have been implicated in creating an increased risk of cardiovascular events and gastrointestinal bleeding. However, these conditions appear to largely occur in persons older than 60 years, those with stomach ulcers or bleeding problems, persons taking blood thinners or steroidal drugs, persons who consume other NSAIDs such as aspirin or naproxen, and persons consuming 3 or more alcoholic drinks every day while using an NSAID.

Commonly known NSAIDs include ibuprofen, aspirin, indomethacin, naproxen, and various salicylate salts.

Ibuprofen (2-(4-isobutylphenyl) propionic acid) is considered to be the safest NSAID on the market today. Amino acid salts of ibuprofen including the lysine or arginine salts are also known pain relievers.

Other well known non-narcotic analgesics include acetaminophen (paracetamol), which is also an antipyretic. While acetaminophen relieves pain, it has no effect on the underlying inflammation, redness and swelling of the joint, and thus is not an NSAID.

Narcotic analgesics such as codeine, hydrocodone, fentanyl, methadone, morphine, oxycodone and propoxyphene provide pain relief, but are generally considered to be habit-forming, and thus are not recommended for frequent consumption.

Caffeine is a well known xanthine alkaloid and is used in a number of foods and medicines. The xanthines, including caffeine, are known to stimulate the central nervous system, induce relaxation of smooth muscle constrictions of the smaller bronchi and other smooth muscles, cause dilation of the small pulmonary arteries, induce stimulation of cardiac muscle with increased cardiac output and the promotion of mild diuresis, and act as vasoconstrictors. It has been postulated that these actions may be related to the antagonism of adenosine receptors.

The B vitamins are water-soluble vitamins that play important roles in cell metabolism. Historically, the B vitamins were once thought to be a single vitamin, referred to as vitamin B. Later research showed that they are chemically distinct vitamins that often coexist in the same foods. Supplements containing all eight are generally referred to as a vitamin B complex. Individual B vitamin supplements are referred to by the specific name of each vitamin (e.g. B1, B2, B6, B12 etc). The B vitamins are necessary in order to support and increase the rate of metabolism; maintain healthy skin and muscle tone; enhance immune and nervous system function; and promote cell growth and division—including that of the red blood cells that help prevent anemia.

The present invention provides a composition or mixture of compositions that comprise analgesics, caffeine and vitamins that are capable of faster onset, enhanced relief as well as longer, extended relief of aches and pains associated with the head and body including migraines and tension headaches. The compositions of the invention cause faster pain relief that lasts longer, thereby allowing a patient to use less of the analgesic components of the composition, thereby reducing side effects.

SUMMARY OF THE INVENTION

In an embodiment, the present invention provides a pharmaceutical composition for use in eliciting an analgesic and/or anti-inflammatory response, the composition comprising an effective amount of an analgesic having an optional anti-inflammatory effect, an amount of caffeine sufficient and an amount of B vitamins sufficient to hasten the onset of the analgesic and/or anti-inflammatory response or to enhance the analgesic and/or anti-inflammatory response. Typically, the active ingredients are further associated with a nontoxic pharmaceutically acceptable inert carrier therefor.

In another aspect, the present invention provides a method of hastening the onset of analgesia or of an anti-inflammatory response in a mammal resulting from administration of an effective amount of an analgesic having an optional anti-inflammatory effect, the method comprising administering to said mammal, the effective analgesic or anti-inflammatory amount of ibuprofen together with an amount of caffeine and an amount of B vitamins sufficient to hasten the onset of analgesia or of the anti-inflammatory response.

In yet another aspect, the present invention provides a method of eliciting an enhanced analgesic or anti-inflammatory response in a mammal, said method comprising administering to said mammal an effective amount of an analgesic having an optional anti-inflammatory effect together with an amount of caffeine and an amount of B vitamins sufficient to enhance the analgesic or anti-inflammatory response, an effective amount of an analgesic having an optional anti-inflammatory effect.

DETAILED DESCRIPTION OF THE INVENTION

This invention claims pharmaceutical compositions for use in the treatment of pain and inflammation. The composition comprises:

(i) an effective amount of an analgesic having an optional anti-inflammatory effect;
(ii) an amount of caffeine effective in enhancement of pain relief; and
(iii) an amount of B vitamins effective in enhancement of pain relief This invention is also directed to a method of treating pain and inflammation in mammals, including humans, in need thereof, comprising administering to such organism:
(i) an effective amount of an analgesic having an optional anti-inflammatory effect; (ii) an amount of caffeine effective in enhancement of pain relief; and, (iii) an amount of B vitamins effective in enhancement of pain relief.

This invention is further directed to a method of eliciting an onset hastened and enhanced response for the treatment of pain and/or inflammation in mammals, including humans, in need thereof, comprising administering to such organism:
an effective amount of an analgesic having an optional anti-inflammatory effect; (ii) an amount of caffeine effective in enhancement of pain relief; and, (iii) an amount of B vitamins effective in enhancement of pain relief.

In certain embodiments of the invention, the compositions of the invention comprise a first composition comprising an analgesic, and a second composition comprising caffeine and B vitamins. In certain embodiments of the invention, the first composition comprises an analgesic that possesses anti-inflammatory properties. In other embodiments of the invention, the first composition comprises an analgesic that does not possess anti-inflammatory properties. In alternate embodiments of the invention, the first composition comprises a non-narcotic analgesic by itself or in combination with a narcotic analgesic.

In an embodiment of the invention, the first composition and second composition are packaged together and dispensed as a kit. In such a kit, the first composition does not comprise caffeine and B vitamins, and the second composition does not comprise an analgesic.

In certain embodiments of the invention, ibuprofen is used as the preferred analgesic/anti-inflammatory compound in the compositions of the invention. Salts of ibuprofen that may used in certain embodiments of the invention include pharmaceutically acceptable salts such as alkali metals (sodium or potassium), alkaline earth metals (calcium), or salts with other metals such as magnesium, aluminum, iron, zinc, copper, nickel or cobalt. Pharmaceutically acceptable salts of ibuprofen further include the amino acid salts, particularly the basic amino acids such as lysine or arginine.

In other embodiments of the invention, a combination of a non-narcotic analgesic and a narcotic analgesic is incorporated in the first composition.

In other embodiments of the invention, other NSAIDs such as naproxen and aspirin may be incorporated in the first composition. In certain embodiments of the invention, either acetaminophen or a combination of acetaminophen and a narcotic analgesic is incorporated in the first composition.

The amount of analgesic used in the compositions of the invention ranges from 100 to 1000 mg.

In certain embodiments of the invention, compositions of the invention may include a buffer, which counteracts any ill-effects of the analgesics, particularly NSAIDs, present in the compositions.

The term mammals or mammalian organism includes but is not limited to man, dog, cat, horse and cow.

The term treatment encompasses the complete range of therapeutically positive effects associated with pharmaceutical medication including reduction of, alleviation of and relief from the symptoms or illness which affect the organism.

Metal salts of ibuprofen may be obtained by contacting a hydroxide, or carbonate with ibuprofen. Amino acid salts of ibuprofen may be obtained by contacting an amino acid in solution with ibuprofen.

The pharmaceutical compositions of the present invention are useful in the rapid and enhanced treatment of pain and inflammation. The combination of analgesics, caffeine and B vitamins provided by the compositions of the invention also have an advantage under circumstances where a mammalian organism requires enhanced pain relief and wakefulness or mental alertness.

Caffeine and B vitamins are used in the invention in combination with the analgesics. The amount of caffeine used in the present invention in humans may range from 20 to 400 milligrams (mg). The B vitamins used in compositions of the invention include vitamin B1 (thiamine), vitamin B2 (riboflavin), vitamin B6 (Pyridoxine HCl) and vitamin B12 (cyanaocobalamin). The amount of vitamins B1, B2 and B6 used in the compositions of the invention may range from 10 mg to 1000 mg. The amounts of vitamin B12 used in compositions of the invention may range from 100 µg to 2 mg.

The B vitamins are vital to a vigorous and energetic long life. The B vitamins are essential for the body's production and use of energy. Consumption of B vitamins provides an energy boost and combats lethargy, in addition to providing pain relief.

The presence of caffeine and B vitamins in the compositions of the invention substantially hastens the onset of analgesia.

In certain embodiments, metals or metal salts may be incorporated in the compositions of the invention to enhance the anti-inflammatory properties of NSAIDs such as ibuprofen. Additionally, these metals or metal salts are capable of reducing the ulcer-causing and other toxic effects of NSAIDs. An example of a metal or metal salt that could be used in the compositions of the invention include copper and its salts.

In other embodiments, licorice or derivatives such as De-Glycyrrhizinated Licorice (DGL) may be used in compositions of the invention. Licorice has long been used as a highly effective alternative to antacids and acid-blocking drugs. By comparison, licorice works not by inhibiting acid production, but rather through supporting and stimulating the stomach's natural protective mechanisms. The incorporation of licorice in compositions of the invention can reduce the ulcer-causing effects and gastrointestinal bleeding that occurs when NSAIDs are consumed by certain individuals.

Consumption of NSAIDs has been shown to interfere with folic acid absorption in certain individuals. Therefore, in certain embodiments, folic acid may be included as an additional component in the compositions of the invention.

The combination claimed in the invention is advantageously administered orally. However, in patients with hypersecretory conditions, intractable ulcers, or in patients who are unable to take oral medication, the claimed combination may be administered intravenously in a suitable dosage within the limits described for oral treatment.

The compositions of the invention may be administered in the form of tablets, caplets, gelcaps, capsules, elixirs, syrups, suspensions, gels and patches. For oral administration, the active ingredients may be admixed with a pharmaceutically acceptable diluent such as lactose, sucrose, cellulose, dicalcium phosphate, calcium sulfate, mannitol, and, in a liquid composition, ethyl alcohol. Acceptable emulsifying or suspending agents such as PVP, gelatin, natural sugars, corn sweeteners, natural and synthetic gums such as acacia, sodium alginate, guar gum, agar, bentonite, carboxymethylcellulose sodium, polyethylene glycol and waxes, may also be admixed with the active components. Where necessary, lubricants such as magnesium stearic acid talc or magnesium stearate, and disintegrators or superdisintegrators such as starch, sodium starch glycolate or cross-linked PVP may also be included. Electrolytes such as dicalcium phosphate, sodium benzoate, sodium acetate and sodium chloride may also be used.

The active components may also be formulated in sustained release or effervescent formulations. These formulations depending upon whether they are sustained release or effervescent may be employed in oral, dermal, rectal or vaginal administrations. The sustained release formulations also include layered formulations which provide for distinct release ratio and thus may be more effective in allowing for short and long term relief.

The nonsteroidal anti-inflammatory drugs for use in the compositions and methods of the present invention can be selected from the following categories:
(1) the propionic acid derivatives;
(2) the acetic acid derivatives;
(3) the fenamic acid derivatives;
(4) the biphenylcarboxylic acid derivatives; and
(5) the oxicams.

While some of these compounds are primarily used as anti-inflammatory agents and others are primarily used as analgesics, in fact all of the contemplated compounds have both analgesic and anti-inflammatory activity and can be used at appropriate dosage levels for either purpose in the compositions and methods of the present invention. The compounds in groups (1) through (4) typically contain a carboxylic acid function; however, those acids are sometimes administered in the form of their pharmaceutically acceptable salts, e.g. sodium salts.

The propionic acid derivatives for use herein include, but are not limited to, ibuprofen, naproxen, benoxaprofen, flurbiprofen, fenoprofen, fenbufen, ketoprofen, indoprofen, pirprofen, carprofen, oxaprozin, pranoprofen, microprofen, tioxaprofen, suprofen, alminoprofen, tiaprofenic acid, fluprofen and bucloxic acid. Structurally related propionic acid derivatives having similar analgesic and anti-inflammatory properties are also intended to be encompassed by this group. Presently preferred members of the propionic acid group include ibuprofen, naproxen, flurbiprofen, fenoprofen, ketoprofen and fenbufen.

Thus, "propionic acid derivatives" as defined herein are nonsteroidal anti-inflammatory drugs having a free —CH(CH$_3$)COOH or —CH$_2$CH$_2$COOH group (which optionally can be in the form of a pharmaceutically acceptable salt group, e.g. —CH(CH$_3$)COO$^-$Na$^+$ or —CH$_2$CH$_2$COO$^-$Na$^+$), typically attached directly or via a carbonyl function to a ring system, preferably to an aromatic ring system.

The acetic acid derivatives for use herein include, but are not limited to, indomethacin, sulindac, tolmetin, zomepirac, diclofenac, fenclofenac, alclofenac ibufenac, isoxepac, furofenac, tiopinac, zidometacin, acemetacin, fentiazac, clidanac and oxpinac. Structurally related acetic acid derivatives having similar analgesic and anti-inflammatory properties are also intended to be encompassed by this group. Presently preferred members of the acetic acid group include tolmetin sodium, zomepirac sodium, sulindac and indomethacin.

Thus, "acetic acid derivatives" as defined herein are nonsteroidal anti-inflammatory drugs having a free —CH$_2$COOH group (which can optionally be in the form of a pharmaceutically acceptable salt group, e.g. —CH$_2$COO$^-$Na$^+$), typically attached directly to a ring system, preferably to an aromatic or heteroaromatic ring system.

The fenamic acid derivatives for use herein include, but are not limited to, mefenamic acid, meclofenamic acid, flufenamic acid, niflumic acid and tolfenamic acid. Structurally related fenamic acid derivatives having similar analgesic and anti-inflammatory properties are also intended to be encompassed by this group. Presently preferred members of the fenamic acid group include mefenamic acid and meclofenamate sodium (meclofenamic acid, sodium salt).

Thus, "fenamic acid derivatives" as defined herein are nonsteroidal anti-inflammatory drugs which can bear a variety of substituents and in which the free —COOH group can be in the form of a pharmaceutically acceptable salt group, e.g. —COO$^-$Na$^+$.

The biphenylcarboxylic acid derivatives for use herein include, but are not limited to, diflunisal and flufenisal. Structurally related biphenylcarboxylic acid derivatives having similar analgesic and anti-inflammatory properties are also intended to be encompassed by this group. Preferred members of this group are diflunisal and flufenisal.

Thus, "biphenylcarboxylic acid derivatives" as defined herein are nonsteroidal anti-flammatory drugs which can bear a variety of substituents and in which the free —COOH group can be in the form of a pharmaceutically acceptable salt group, e.g. —COO$^-$Na$^+$.

The oxicams for use herein include, but are not limited to, piroxicam, sudoxicam, isoxicam and CP-14,304. Structurally related oxicams having similar analgesic and anti-inflammatory properties are also intended to be encompassed by this group. A preferred member of this group is piroxicam.

The term "caffeine" as used herein is intended to encompass not only caffeine as the anhydrous powder, but any salt or derivative of caffeine or any compounded mixture thereof which is non-toxic, pharmaceutically acceptable and which is capable of hastening and enhancing an analgesic or anti-flammatory response when employed as described herein. See, for example, The Merck Index, ninth edition, Merck & Co., Inc. Rahway, N.J. (1976), pp. 207-208, for a description of caffeine salts, derivatives and mixtures which may prove useful in the compositions of the present invention. Nevertheless, caffeine as the anhydrous powder base is presently preferred and, where specific amounts of caffeine are set forth below, such amounts are given in mg of the anhydrous base.

The term "selected analgesic" as used herein is intended to mean any analgesic, whether narcotic or non-narcotic, as well as nonsteroidal anti-inflammatory compounds falling within one of the five structural categories indicated hereinabove. The term "selected analgesic" is used for the sake of simplicity in the discussion which follows.

For patients suffering pain, the time from administration of medication to the onset of effective relief is clearly of paramount importance. The presence of caffeine and B vitamins substantially shortens the onset time (i.e. substantially hastens the onset) of analgesia and is therefore very significant. Likewise, in patients suffering inflammation, e.g. from rheumatoid arthritis or osteoarthritis, the substantial shortening of onset time provided by this invention is extremely important, not only because it provides faster relief from pain but also because provides more rapid relief from other aspects of the inflammatory disease, e.g. morning stiffness.

More specifically, it is believed that onset time for analgesia or for the anti-inflammatory response can be reached, on the average, about one-fourth to about one-third sooner when a composition of the invention is used rather than when the selected analgesic alone is employed. Also, approximately one-fifth to one-third less of the selected analgesic can be used in the combination composition of the invention, i.e., with caffeine and B vitamins, to achieve the same analgesic or anti-inflammatory effect as that obtained by use of the selected analgesic alone; in other words, the addition of caffeine and vitamins decreases the amount of the selected analgesic to about two-thirds to four-fifths of the usual amount to achieve the same effect with longer relief, and thereby reduces the side effects of the analgesics being used, particularly NSAIDs. These ratios may vary, however, depending on the patient's individual response, the selected dosage level of the active ingredients etc.

In certain embodiments of the invention, a method of treating pain and inflammation and enhancing pain relief in a mammalian organism in need of such treatment is provided. The method comprises the steps of administering to the organism, a first composition comprising an effective amount of an analgesic; and a second composition comprising an amount of caffeine effective in the enhancement of pain relief and an amount of B vitamins effective in the enhancement of pain relief, wherein the first composition does not contain caffeine or B vitamins and the second composition does not contain analgesic, and further wherein the first composition and the second composition are always administered contemporaneously to the organism. In other words, the first composition and the second composition must be administered to or consumed by the organism at the same time in order for the organism to obtain the enhanced pain relief provided by the compositions of the invention. However, the order in which the first composition and second composition are administered to the organism is not material; rather it is important that both the first and second compositions are administered contemporaneously to the organism. Furthermore, the ratio of the first composition to the second composition can be 1:1, 1:2, 1:3 respectively, which allows the amount of analgesic to be maintained at a constant level, while enhancing and extending the level of pain relief by increasing the amounts of the second composition comprising caffeine and B vitamins. Thus, extended and enhanced pain relief is achieved without the side effects that are commonly encountered with increased consumption of analgesics such as NSAIDs.

In other embodiments of the invention, a method of eliciting an onset enhanced and hastened response or the treatment of pain and inflammation and the enhancement of pain relief in a mammalian organism in need of such treatment is provided. The method comprises the steps of administering to the organism, a first composition comprising an effective amount of an analgesic; and a second composition comprising an amount of caffeine effective in the enhancement of pain relief and an amount of B vitamins effective in the enhancement of pain relief, wherein the first composition does not contain caffeine or B vitamins and the second composition does not contain analgesic, and further wherein the first composition and the second composition are always administered contemporaneously to the organism. In other words, the first composition and the second composition must be administered to or consumed by the organism at the same time in order for the organism to obtain the enhanced pain relief provided by the compositions of the invention. However, the order in which the first composition and second composition are administered to the organism is not material; rather it is important that both the first and second compositions are administered contemporaneously to the organism.

Compositions of the invention allow a patient to obtain extended or enhanced relief of the pain they are experiencing by varying the intake of caffeine and B vitamins relative to the amount of analgesic that is consumed. For example, an embodiment of the invention allows a patient to consume a fixed amount of a first composition comprising an analgesic, while varying the amount of the second composition comprising caffeine and B vitamins. In so doing, the patient experiences an enhanced level of pain relief as well as an extended period of pain relief, without needing to increase the amount of analgesic at the same time. Because the increased use of analgesics, particularly NSAIDs, can cause patient discomfort and additionally is not recommended because of side effects. Therefore, embodiments of the invention provide a user the ability to obtain enhanced and extended pain relief without ingesting additional analgesics to obtain the desired pain relief.

In an embodiment of the invention, a patient is able to obtain enhanced and extended pain relief by increasing the amount of the composition comprising caffeine and B vitamins, while keeping the amount of analgesic constant. Thus, compositions of the inventions may be used by persons of all age groups and health conditions, with fewer side effects, because the amount of analgesic required to be consumed for adequate pain relief may be maintained at a safe, constant amount, while consuming increasing amounts of the composition comprising caffeine and B vitamins as needed.

For example, a teenage girl suffering from menstrual cramps may require 400 mg of ibuprofen in conjunction with a single dose of the second composition comprising caffeine and B vitamins, in order to relieve her pain. On the other hand, an older woman suffering from menstrual cramps that cause more discomfort and fatigue, might wish to consume a double dose of the second composition comprising caffeine and B vitamins along with 400 mg of ibuprofen, in order to obtain pain relief and an energy boost from the B vitamins. Furthermore, a patient suffering from a tension headache, characterized by dilated blood vessels, might consider taking three doses of the second composition comprising caffeine and B vitamins, in order to deal with the pain and to cause constriction of blood vessels around the skull through the use of caffeine.

The precise amount of nonsteroidal anti-inflammatory drug for use in the present compositions will vary depending, for example, on the specific drug chosen, the condition for which the drug is administered and the size and kind of the mammal. Generally speaking, the selected NSAID can be employed in any amount known to be an effective analgesic or anti-inflammatory amount, as well as at doses one-fifth to one-third lower than the usual amounts.

For humans, typical effective analgesic amounts of presently preferred NSAIDs for use in unit dose compositions of the invention are about 125 to 500 mg diflunisal, about 25 to 100 mg zomepirac sodium, about 50 to 800 mg ibuprofen, about 125 to 500 mg naproxen, about 25 to 50 mg flurbiprofen, about 50 to 200 mg fenoprofen, about 10 to 20 mg piroxicam, about 125 to 250 mg mefenamic acid, about 100 to 400 mg fenbufen or about 25 to 50 mg ketoprofen; however, greater amounts can be employed if desired. The amount of caffeine in the analgesic composition will be an amount sufficient to shorten the onset time and/or to enhance analgesia. For humans, a unit dosage analgesic composition will typically contain from about 60 to about 200 mg (preferably about 65 to about 200 mg) caffeine; this dosage level of caffeine is generally sufficient to both shorten the onset time and enhance analgesia. However, certain NSAIDs are particularly long-acting and need be administered less frequently than the usual every 4 to 6 hours; for example, diflunisal and naproxen are typically administered only twice daily and piroxicam only once a day. When such long-acting drugs are employed, it is often desirable to include an additional analgesia-enhancing amount of caffeine in the composition in sustained release form; thus, the composition will typically contain from about 60 to about 200 (preferably about 65 to about 200) mg caffeine for immediate release to hasten onset and enhance analgesia, and one (or possibly more) additional 60 to 200 (preferably 65 to 200) mg dose(s) of caffeine for sustained release to continue enhancement of analgesia. The daily analgesic dose in humans will vary with the selected NSAID, and may of course be as low as the amount contained in a single unit dose as set forth above. The daily dose for use in the treatment of mild to moderate pain will preferably not exceed 1500 mg diflunisal or 600 mg zomepirac sodium or 2400 mg ibuprofen or 1000 mg naproxen or 150 mg flurbiprofen or 2400 mg fenoprofen or 20 mg piroxicam or 1000 mg mefenamic acid or 2400 mg fenbufen or 300 mg ketoprofen, plus 1000 mg caffeine, for use in the treatment of mild to moderate pain, although greater amounts could be employed if tolerated by the patient.

While the compositions of the invention are preferably for oral use, they may also be formulated for and administered by other methods which are known for administering analgesics, e.g. as suppositories. Also, the preferred human dosage levels indicated above are for use in adults; pediatric compositions would contain proportionately less of the active ingredients.

The compositions of the present invention are very conveniently administered to mammals by any route of administration suitable for the selected NSAID e.g. oral or rectal. Preferably, the combination is formulated with any suitable nontoxic pharmaceutically acceptable inert carrier material. Such carrier materials are well known to those skilled in the art of pharmaceutical formulations. For those not skilled in the art, reference is made to the text entitled, "REMINGTON'S PHARMACEUTICAL SCIENCES" (Fourteenth Edition), 1970. In a typical preparation for oral administration, e.g., tablet or capsule, the selected NSAID in an effective analgesic or anti-inflammatory amount and caffeine in an amount sufficient to enhance the analgesic or anti-inflammatory response or to hasten its onset, and a vitamin in an amount sufficient to enhance the analgesic or anti-inflammatory response or to hasten its onset, are combined with any oral nontoxic pharmaceutically acceptable inert carrier such as lactose, starch (pharmaceutical grade), dicalcium phosphate, calcium sulfate, kaolin, mannitol and powdered sugar. Additionally, when required, suitable binders, lubricants, disintegrating agents and coloring agents can also be included. Typical binders include starch, gelatin, sugars such as sucrose, molasses and lactose, natural and synthetic gums such as acacia, sodium alginate, extract of Irish moss, carboxymethylcellulose, methylcellulose, polyvinylpyrrolidone, polyethylene glycol, ethylcellulose and waxes. Typical lubricants for use in these dosage forms can include, without limitation, boric acid, sodium benzoate, sodium acetate, sodium chloride, leucine and polyethylene glycol. Suitable disintegrators can include, without limitation, starch, methylcellulose, agar, bentonite, cellulose, wood products, alginic acid, guar gum, citris pulp, carboxymethylcellulose and sodium lauryl sulfate. If desired, a conventional pharmaceutically acceptable dye can be incorporated into the dosage unit form, i.e., any of the standard FD&C dyes. Sweetening and flavoring agents and preservatives can also be included, particularly when a liquid dosage form is formulated, e.g. an elixir, suspension or syrup. Also, when the dosage form is a capsule, it may contain, in addition to materials of the above type, a liquid carrier such as a fatty oil. Various other materials may be present as coatings or to otherwise modify the physical form of the dosage unit. For instance, tablets, pills, or capsules may be coated with shellac, sugar or both. Such compositions should preferably contain at least 0.1% of active components; generally, the active ingredients will be between about 2% to about 60% of the weight of the unit.

The following examples illustrate the compositions of the present invention which may be readily prepared and as such are not to be considered as limiting the invention set forth in the claims.

EXAMPLE 1

A kit comprising a first composition comprising 800 mg of ibuprofen and a second composition comprising 65 mg of caffeine, 25 mg of thiamine, 6.25 mg of riboflavin, 25 mg of pyridoxine HCl and 125 µg of cyanocobalamin. Other ingredients used in the first and second compositions include maltodextrin and magnesium stearate.

A first tablet comprising the first composition and a second tablet comprising the second composition are administered to a patient to alleviate pain or a combination of symptoms of pain and inflammation.

From the foregoing description, one of ordinary skill in the art can easily ascertain the essential characteristics of the invention, and without departing from the spirit and scope thereof, can make various changes and/or modifications of the invention to adapt it to various usages and conditions. As such, these changes and/or modifications are properly, equitably and intended to be, within the full range of equivalence of the following claims.

The invention claimed is:

1. A pharmaceutical kit for use in the treatment of pain and inflammation and the enhancement of pain relief in mammals, including humans comprising:
   a first composition comprising an effective amount of an analgesic; and
   a second composition consisting of caffeine and B vitamins, wherein the first composition does not contain caffeine or B vitamins and the first composition and the second composition are separately packaged in a kit as a unit dose of the first composition and a unit dose of the second composition and the number of dispensed unit doses of the first composition is independent of the number of dispensed unit doses of the second composition, wherein the first composition and the second composition are dispensed simultaneously, and wherein the first composition is dispensed at a fixed amount, while the second composition is dispensed at varying amounts relative to the first composition, for the enhanced relief of pain for an extended duration.

2. The pharmaceutical kit of claim 1, wherein the first composition comprises an NSAID.

3. The pharmaceutical kit of claim 1, wherein the first composition comprises a non-narcotic analgesic.

4. The pharmaceutical kit of claim 2, wherein the first composition comprises at least 50 mg of an NSAID selected from the group consisting of ibuprofen, aspirin and naproxen.

5. The pharmaceutical kit of claim 1, wherein the amount of caffeine ranges from 20-400 mg.

6. The pharmaceutical kit of claim 1, wherein the amount of B vitamins range from 10 mg to 1000 mg and the B vitamins are selected from the group consisting of B1, B2 and B6.

7. The pharmaceutical kit of claim 4, wherein the first composition comprises 100-400 mg of ibuprofen.

8. The pharmaceutical kit of claim 4, wherein the first composition comprises 100-800 mg of ibuprofen.

9. The pharmaceutical kit of claim 1, wherein the amount of caffeine ranges from 32-400 mg.

10. The pharmaceutical kit of claim 1, wherein the amount of B vitamins range from 100 µg to 1000 mg.

* * * * *